United States Patent [19] … [11] Patent Number: 6,153,375
Kobylecki et al. … [45] Date of Patent: *Nov. 28, 2000

[54] METHOD OF MAKING A LIBRARY OF COMPOUNDS USING A FUNCTIONALIZED POLYMER SUPPORT RESIN AFFIXED TO A LAMINAR MATERIAL

[75] Inventors: Ryszard Jurek Kobylecki; John Mark Francis Gardner, both of Sandwich, United Kingdom

[73] Assignee: Cambridge Combinatorial Limited, Castle Park, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,755

[22] PCT Filed: Nov. 17, 1995

[86] PCT No.: PCT/GB95/02707

§ 371 Date: May 16, 1997

§ 102(e) Date: May 16, 1997

[87] PCT Pub. No.: WO96/16078

PCT Pub. Date: May 30, 1996

[30] Foreign Application Priority Data

Nov. 18, 1994 [GB] United Kingdom ............... 9423332

[51] Int. Cl.[7] ............... C12Q 1/00; G01W 33/53
[52] U.S. Cl. ............... 435/4; 435/7.1; 436/518; 436/536; 436/8; 536/23.1; 536/25.3; 530/333; 530/334
[58] Field of Search ............... 435/7.1, 4, DIG. 49; 436/518, 536; 431/8; 536/23.1, 25.3; 530/333, 334

[56] References Cited

FOREIGN PATENT DOCUMENTS

WO 92/10092 6/1992 WIPO .
WO 93/06121 4/1993 WIPO .
WO94/05394 3/1994 WIPO .
WO 95/05475 2/1995 WIPO .
WO 95/30026 11/1995 WIPO .
WO 95/32307 11/1995 WIPO .
WO 93/06121 4/1997 WIPO .

OTHER PUBLICATIONS

Eichler, J. et al Collect. Czech. Chem. Commun. 54: 1746–1752, 1989.

Frank, R. and Doring, R. Tetrahedron 44(19): 6031–6040, 1988.

Frank, R., et al., Nucleic Acids Research 11(13) 4365–4377, 1983.

Frank, R. Bioorganic & Medicinal Chem. Lett. 3(3) 425–430, Mar. 8, 1993.

Gallop et al. Applications of Combinatorial Technologies to Drug Discovery 1. J. Med. Chem. 37:(9) 1233–1251, Apr. 29, 1998.

Lam et al The chemical synthesis of large random peptide libraries and thier use for the discovery of ligands for macromolecular acceptors. Bioorganic & Med. Chem. Lett. 3(3) : 419–424, 1993.

Stankova et al. Synthesis of combinatorial libraries with only one representation of each structure. Peptide Res. 7(6): 292–298, 1944.

Frank, R. (1993) Bioorg. Med. Chem. Lett. 3:425–30.

Desai et al. (1994) Drug Dev. Res. 33:174–88.

Lee et al. (1995) Chem. Abst. 123:1251(No. 340780z).

Young et al. (1995) Chem. Abst. 123:844 (No. 55067r).

Primary Examiner—Bennett Celsa
Assistant Examiner—Joseph W. Ricigliano
Attorney, Agent, or Firm—Jack Matalon

[57] ABSTRACT

The instant invention is directed to a method of making a library of compounds using a segmentable support material comprised of a particulate resin affixed to a porous laminar material.

19 Claims, 1 Drawing Sheet

METHOD OF MAKING A LIBRARY OF COMPOUNDS USING A FUNCTIONALIZED POLYMER SUPPORT RESIN AFFIXED TO A LAMINAR MATERIAL

This application is a 371 of PCT/GB95/02707 and claims priority to GB 9423332.7.

BACKGROUND OF THE INVENTION

The present invention relates to a method of preparation of chemical compounds and, in particular, to a method of preparing combinatorial libraries of chemical compounds. The method is especially suitable for the preparation of natural and synthetic chemical compounds which are to be tested for activity as therapeutic agents, though it need not be used exclusively for this purpose. In addition to being used for the preparation of combinatorial libraries, the method of the present invention also facilitates easy identification of individual compounds, so that any compounds which show encouraging biological activity can be prepared on a larger scale for further analysis. By modifying the method of the present invention, it is possible to prepare individual compounds in pure form in a non-combinatorial format.

The synthesis and screening of combinatorial libraries is becoming increasingly important in the pharmaceutical industry as a means of drug "discovery". The major advantages of combinatorial chemistry are that it is faster and cheaper than orthodox methods. This makes it a much more effective technique in the quest to uncover new therapeutic agents, particularly in circumstances where there is little or no information available concerning the types of structures likely to show the desired activity.

The wider availability of solid-phase synthetic methods has also led to increased interest in combinatorial chemistry. Clearly, solution chemistry is unsuitable for a technique which aims to produce a multiplicity of new products together, since this does not allow physical separation between the different materials produced. The products are therefore likely be contaminated with excess reagents, by-products etc, leading to difficulties in separation and purification.

The preparation of combinatorial compound libraries typically involves a number of successive stages, each of which involves a chemical or enzymatic modification of an existing molecule. Most typically, this process involves the addition of a monomeric unit or other synthon to a growing sequence, or the modification of chemical functionality on the sequence. Conveniently, the sequence or growing chain of interest is attached to a solid support. By carrying out the desired series of synthetic steps on the bound starting material, and by altering the nature of the monomeric or other synthon units, the type of chemistry and the sequence of reactions, it is possible to prepare an enormous number of individual compounds in short time.

As indicated above, combinatorial methods entail a series of chemical steps with multiple choices of chemical reagents for each step. The complexity of the combinatorial library thus produced is determined by the product of the number of reagent choices for each step of the synthesis, which can be quite large. The problem which then arises is identification and characterisation of members of the library which display particular desired properties.

Various solutions have been proposed to deal with this: For example, members of the library can be synthesised in spatially segregated arrays. However, because of the extra burden which maintenance of segregation imposes, this approach tends to lead to relatively small libraries. Alternatively, in the so-called "multivalent synthesis" method, a library of moderate complexity is produced by pooling multiple choices of reagents during synthesis. If a pool is shown to have properties of interest, it is re-synthesised with progressively lower complexity until a single compound or class of compounds is identified having the desired property. The ultimate size of a library produced by this technique is inevitably restricted because of concentration effects which determine the limits of detection at which activity can be discerned.

The so-called "mix and split synthesis" method relies on combinatorial synthesis carried out on discrete solid particles such as minute resin beads. Through a protocol of mixing and separating beads at the end of each step in the synthetic sequence, populations of beads are generated to which are bound the products of specific reaction sequences. Inevitably, individual beads obtained from the final reaction step have different products attached, so that identification and characterisation of active materials is still a problem.

Fortunately, biologically active compounds show remarkable potency and receptor sites are highly selective, so it is possible to detect low concentrations of active compound amid an extensive background of inactive material using standard in vitro screening techniques.

Another drawback of the mix and split synthesis method is that some measure of over-representation and omission of individual compounds is inevitable because of the randomness introduced by the mixing and splitting steps.

To counteract the above problems of identification and characterisation, some workers have proposed co-synthesis of a sequencable tag which encodes the series of steps and reagents used during synthesis of respective constituents of the library. More recently, it has been proposed to use tagging molecules to encode both the step number and the chemical reagent used in a given step, as a binary record of the synthetic steps experienced by each bead. This technique undoubtedly adds to the complexity of operations carried out during development of a combinatorial library.

From the foregoing, it is apparent that known methods of preparing combinatorial libraries of chemical compounds suffer from two major drawbacks: Either the materials are prepared by maintaining segregation, with the inevitable consequence that only relatively small libraries are practicable, or the materials are prepared without segregation but in such minute quantities that characterisation is rendered very difficult.

SUMMARY OF THE INVENTION

It is therefore an object of the present invention to provide a method of making a library of chemical compounds which allows wide diversification in the products obtained without over-representation and/or omission, at the same time as providing a clear indication of the sequence of steps which has been followed to synthesise a particular compound, thereby facilitating characterisation of individual materials.

In a first aspect, the invention is a method of making a library of compounds, which method comprises the following steps:

(a) individually marking with indicia a plurality of discrete reaction zones defined on laminar solid support material;

(b) charging each of said reaction zones with a starting material;

(c) sub-dividing the reaction zones into at least two initial batches;

(d) applying at least two different reagents, one to each of the reaction zones in each initial batch, and recording the identity of those reaction zones to which each of said different reagents is applied;

(e) subjecting all reaction zones to reaction conditions which promote reaction to completion;

(f) further sub-dividing the reaction zones into at least two alternative batches;

(g) applying at least two different reagents, one to each of the reaction zones in each alternative batch, and recording the identity of those reaction zones to which each of said different reagents is applied;

(h) subjecting all reaction zones to reaction conditions which promote reaction to completion, and (i) repeating steps (f) to (h) inclusive from zero to n times, as desired.

It will be understood that n may be any whole number integer, the value of which depends on the complexity of the combinatorial library that it is intended to produce.

The method outlined above provides the synthetic chemist for the first time with the means to synthesise any number of single, easily identifiable labelled chemical compounds on a controllable pre-defined scale of preparation. In particular, this invention offers considerable handling advantages over prior art methods. For example, if desired the entire set of individual reaction zones may be handled as a single laminar medium. This opportunity does not exist with free-flowing microscopic resin beads. The method of division does not rely on the laminar support material being a particular shape. Thus, it is possible for the support to be in the form of tapes or streamers.

In an especially preferred form, the reaction zones are defined on sheets of material. An individual sheet may represent a single reaction zone, in which case a plurality of sheets is required to put the invention into effect. Alternatively, a single sheet may be sub-divided into an array of reaction zones of equal size, individual elements of the array being separable from each other for effecting step (c) above. In one possible variant of this method, each sheet is charged with a different starting material in step (b).

An especially preferred form of sheet material is paper, particularly paper which has been treated to enable the starting material to bind to the sheet. When the starting materials are amino acids or peptide fragments, the paper may for example carry allylic anchor groups to releasably bind the carboxylic acid groups of amino acids to the paper; a variety of other linking groups is also possible. The first and subsequent reagents may attach further amino acids or peptide fragments to the already bound amino acid residues on the sheet in known manner.

Another type of paper which may be used has free amino groups which may releasably bind to carboxy groups of amino acids forming the starting material of the library compounds. One method of making such a paper is to treat cellulose, preferably in powder form, with acrylonitrile and a base, generally under aqueous conditions, to form a cyanoethyl ether of cellulose. The product may be dried and reduced, for example with borane in tetrahydrofuran, to aminopropyl cellulose. After removal of residual reagents the amino groups may be protected, for example by conversion of the aminopropyl groups to tert-butyloxycarbonyl aminopropyl groups and the resulting substituted cellulose may be mixed with cellulose fibre and formed into paper by standard paper-making methods.

The tert-butyloxycarbonyl or "Boc" groups may then be removed to provide the required paper with free amino groups.

In a second aspect, the invention is a method of preparing a paper support material for use in the synthesis of chemical compound libraries, which method comprises:

(a) linking cellulose with a compound which is selected from the set consisting of an amine precursor or a compound having a protected amine group;

(b) in the case of an amine precursor, generating the free amine and then protecting it with a conventional amino protecting group;

(c) incorporating the amine-functionalised cellulose into a paper sheet by mixing with paper fibre and forming into sheets, and (d) reacting the paper sheets obtained from step (c) above with an amino deprotecting reagent to provide free amine groups on the paper sheets.

Alternatively, materials other than paper may be used for making the sheets. This is an important consideration for those branches of chemistry which require a non-protic environment, since paper is a protic material.

One possible alternative is a polyethylene or polypropylene film which has been grafted with polystyrene chains, as described in published PCT Patent Application No. WO 90/02749. Alternatively, the sheet may be of a laminated construction, being in the form of a solid material trapped between two or more layers of porous mesh. One laminate of this type consists of a so-called "resin cloth" comprising cross-linked polystyrene resin containing amino groups formed as a layer sandwiched between fibrous sheets, for example, non-woven polypropylene sheets, on which indicia may be borne. The use of other materials is, of course, possible.

A non-protic sandwich material such as that described above permits a wider range of chemistries to be carried out. For example, chemistry is permitted to be performed on a supported resin cloth which usually requires strictly anhydrous conditions. Example reactions include, but are not limited to, use of a strong non-protic base to generate anions of chemical substrates affixed to the resin cloth. Further manipulations of these anions permits, for example, Heck type couplings, Stille couplings, heteroaryl couplings, carbonylations, carboxylations and carbamoylations not normally permitted in a protic environment.

In a third aspect, the invention is a method of preparing a laminar resin support material for use in the synthesis of chemical compound libraries, which method comprises affixing a layer of particulate functionalised solid support resin material to a porous inert laminar material.

Preferably, the layer of particulate functionalised solid support resin material is sandwiched between two layers of porous inert laminar material.

In general, suitable sheet material may be any material which is readily markable with indelible indicia, is divisible in equal proportions, allows the sheets to be formed into a stack and subsequently separated and to which the constituents of the compounds of the library may releasably be bound. The sheet and method of binding the compounds are preferably such that known amounts of the compound may be repeatably released from a single sheet portion bearing the compound.

It should be noted that the present invention is not limited to the preparation of biologically active compounds. It is applicable to any organic or inorganic species which, used in combination with other reagents, will form oligomers bound to the solid sheet. The compounds which are stored in the library must however be compatible with the material of the sheet.

Besides sheet materials, any suitable support material can be adapted for use in the method of the present invention provided that it has the capacity for division and subsequent sub-division into discrete reaction zones and provided that it possesses the necessary surface active qualities to serve as a vehicle for the intended reaction steps.

The compounds prepared in the library may be linked to the support by a wide variety of methods, depending on the nature of the support and the compounds to be prepared. Apart from the allylic anchoring group/amino acid system mentioned above, chemical linkers which may be cleaved by acidic, basic, hydrogenolytic or other chemical reagents may be used, as may light-induced cleavage. Combinations of these methods may also be used.

The amount of compound stored in each reaction zone may vary according to the nature of the compound and the nature of the support material, and also according to the size of the zones. Amounts of compound varying from a few nanograms to several milligrams may be stored on portions of paper sheet of convenient size. In principle any amount of compound may be stored provided that the support material is large enough.

Typically, the different reagents used in the method according to the present invention are individual monomeric units and may be chosen from a large variety of compounds. These include agents such as amino acids, nucleotides, sugars, naturally-occurring and synthetic heterocycles, lipids, and combinations thereof, though it will be understood that this list is not exhaustive. In general, any bifunctional group may be used which may be linked to the support material or to the growing sequence in protected form, and subsequently deprotected and reacted with a further group. Alternatively, a monofunctional group may be used to complete the sequence.

It is an essential feature of the present invention that individual reaction zones are identified, that is to say, labelled with some form of indicia which uniquely characterises each reaction zone. The indicia may comprise, for example, numbers, letters, symbols or colours in a coded combination. The indicia may be applied to the respective reaction zones before synthesis commences using known printing methods. These are preferably such that the ink used will not leach out of the reaction zones during the synthetic procedures, or otherwise interfere with formation and subsequent removal of a compound held on a particular reaction zone. U.V.-sensitive ink which is "fixed" to the reaction zones by exposure to ultraviolet radiation after printing is generally suitable for this purpose. Other types of indicia, not necessarily optical in nature, may be used for identifying individual reaction zones. Possible alternatives include Smiles strings, bar-codes, chemical structures, marked or printed punched card formats, ultraviolet-readable fluorescent systems and electro-magnetically readable devices such as magnetic strips. The type of indicia used may depend on the size and shape of the support material and/or reaction zones.

BRIEF DESCRIPTION OF THE DRAWINGS

FIG. 1 shows a schematic of one form of the support material.

DETAILED DESCRIPTION OF THE INVENTION

Figure 1:
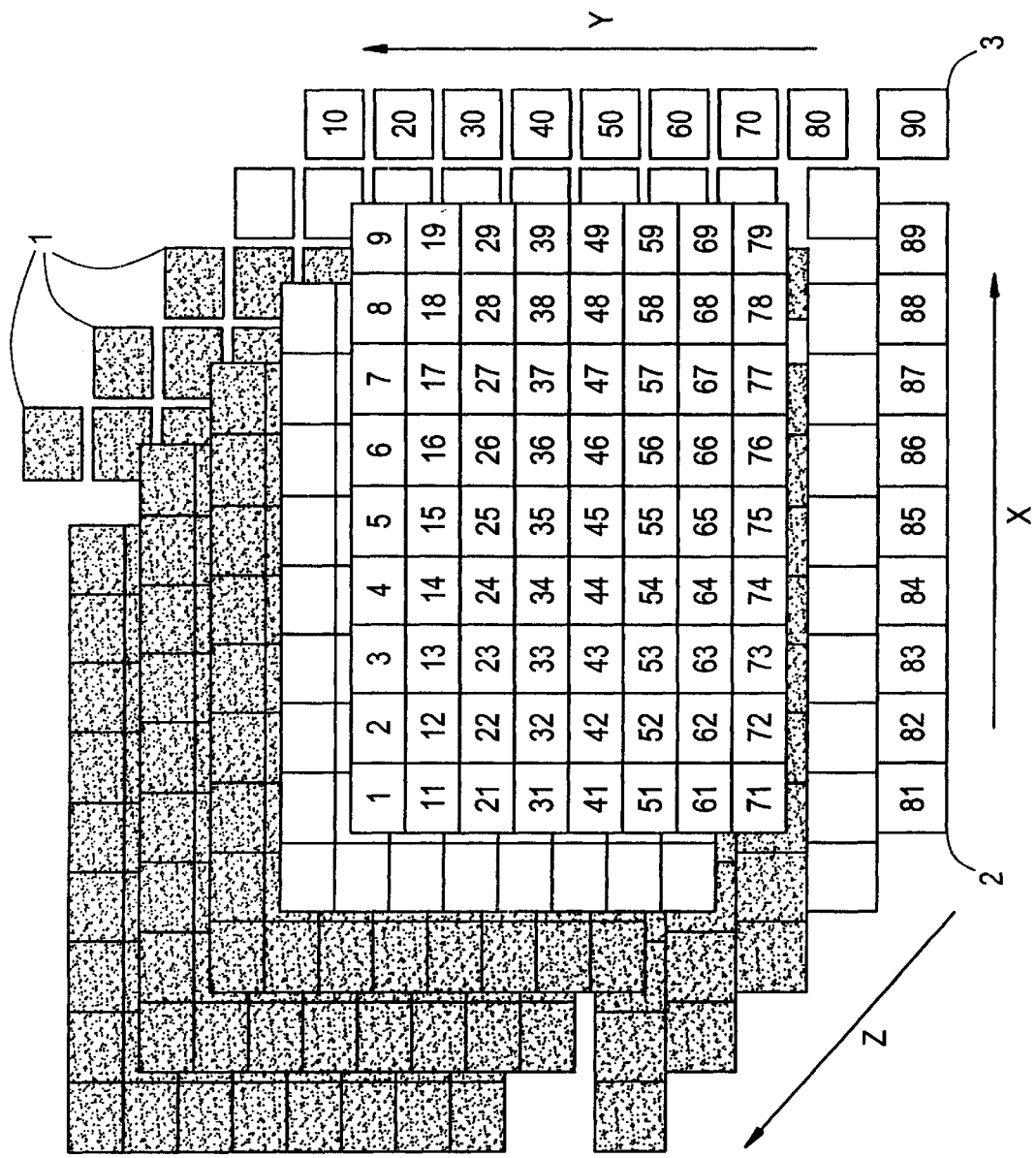
FIG. 1.

The invention will now be described by way of example only with reference to the drawing (FIG. 1) which shows in schematic form one particular embodiment of support material used in performance of the present invention and a convenient pattern of sub-division.

Referring now to FIG. 1, the illustrated arrangement shows orthogonal arrays of reaction zones 3 defined on a series of support sheets 1. The reaction zones are arranged in a grid or matrix layout in straight rows along one dimension and straight columns along the other dimension, each reaction zone being provided with a unique tag or label.

In the next step, each of the sheets 1 is treated with a different first reagent which becomes bound to the sheet to form the first monomer or constituent serving as the starting material for subsequent steps. The sheets are then superposed to form a block in which corresponding reaction zones 3 of respective sheets are aligned with each other. The block of sheets so formed is then divided by making a first series of cuts through the stack, e.g. in the X direction, thereby forming a plurality of stacked strips 2.

Each stack of strips 2 is then treated with a reagent to effect deprotection or activation of the first constituent following reaction with a different second reagent to effect binding of a respective second constituent to the first constituents already bound on the strips.

Following this, the treated stacks of strips are reassembled to reform the block and a second series of cuts is made at right angles (in the Y direction) to the first so that each strip becomes further sub-divided into smaller elements corresponding to the reaction zones (3).

Each of the stacks of individual reaction zones is then deprotected if necessary and treated with a different third reagent to effect binding of a respective third constituent on the free end of the second constituent already in place.

If, in this example, a total of twenty sheets is used initially and if each sheet is treated with a different first reagent monomeric unit, twenty different sheets having attached a first monomer or fragment will be formed. When the superposed sheets are divided to form, say, 20 strips and each strip is treated with a different reagent a total of 20×20=400 dimeric chains is formed, each having a different combination of first and second monomers or fragments. Subsequent reassembly of the block and further sub-division along the second dimension into, say, 20 slices and treatment of each of the slices with different reagents will give 20×20×20=8,000 different pure trimeric structures. The total number of monomers, dimers and trimers may be increased by dividing the block into a greater number of strips or slices, or by increasing the number of sheets. Thus, if 50 sheets are used, divided into 50 strips and 50 slices, the number of different pure individual trimeric structures will be 125,000.

Each of the trimers will be different and will be identifiable unambiguously from the indicia (which may be letters and/or numbers applied by printing) marked on the reaction zones.

At this final stage of the process, the sheets have been cut in a fashion to provide individual pieces of paper, each of which is marked with a single, unique index, which is in itself an identifier of the single, unique chemical structure attached to that portion of paper. Furthermore, all possible combinations are formed of compounds available from the constituents provided by the reagents used.

In the embodiment of the invention described above, the reaction zones may be square or oblong and arranged in an orthogonal pattern. However, other geometrical arrangements may be used. In principle the sheet portions may be of any shape and arranged in any type of grid pattern, subject only to the need to divide the sheet into individual portions.

The sheet material may be, but is not limited to, paper and depending on the size of the sheets cutting may be carried out using any suitable cutting device, such as scissors or an ordinary office guillotine. The arrangement described above allows a very large number of different dimeric and trimeric and larger polymeric structures to be assembled easily and rapidly.

It will be apparent that in a library of single individual compounds, each of which is identified by means of its own unique indicia, an individual sheet portion may be easily identified. Thus, evaluation of the biological or other activity of the compound cleaved from such an identified sheet portion will permit, by means of targeted screening of structurally related compounds, a search for activity by substructure within a library generated by a combinatorial method.

The method of making a library of compounds described above may be considered as starting with a three-dimensional stack of sheets which is divided three times in different dimensions (once by separating the sheets, and twice by cutting) and treating with three different sets of reagents. The same principle may be applied to a two-dimensional system using a single sheet which is divided twice in two transverse directions and treated with two reagents.

Such an arrangement still allows provision of a large number of compounds in a library. For example, if a single sheet is divided into a pattern consisting of 50×50 squares a total of 2500 different compounds, each of known composition and unambiguously identified, may be obtained. In another embodiment, the sheets may be in the form of tape or streamers which comprise only a single line of reaction zones which are separated by cutting in the transverse direction. These tapes or streamers bearing a one-dimensional array of reaction zones may be superposed to form a block which is treated and subdivided in a manner similar to that described above.

It will also be appreciated that the block of sets of individual reaction zones may be further divided and reacted with a fourth or subsequent set of reagents to provide a further dimension of product variation.

In general, the invention is applicable to any arrangement of sheet material in which both the "sheets" and the reaction zones defined thereon may, after sub-division, be handled and subjected to the desired chemical process steps without losing their physical integrity or their identifying indicia. The manner in which the sheets are divided into portions (cutting, stamping, tearing etc.) will depend on the identity of the sheet material and the shape and size of the reaction zones.

The invention is further illustrated by the non-limiting examples described below, in which the following abbreviations are used:
Fmoc: 9-Fluorenylmethoxycarbonyl
Boc: Tert-butyloxycarbonyl
THF: tetrahydrofuran
DMF: N,N-dimethylformamide
TFA: trifluoroacetic acid
HOBt: N-1-hydroxybenztriazole
TBTU: 2-(1H-benzotriazole-1-yl)-1,1,3,3-tetramethyluronium tetrafluoroborate
Hunig's base: N,N-diisopropylethylamine

EXAMPLE 1

Syntheses conducted on Boc-aminopropyl cellulose sheet
Preparation of cyanoethyl cellulose:

A suspension of 70% water wet-partially cross-linked cellulose powder (XEC Whatman) 13 kg was suspended in dioxan (28 l), and treated with a solution of sodium hydroxide (210 g) in water (200 ml) and the viscous suspension stirred at room temperature for 10 min. Acrylonitrile (201.5 g, 250 ml, 3.79 mole) was added, the mixture stirred 5 min, further acrylonitrile (201.5 g, 250 ml, 3.79 mole) was added, the mixture stirred 5 min, and thereupon a final portion of acrylonitrile (403 g, 500 ml, 7.95 mole) was added and the whole reaction mixture stirred at room temperature for a total of 5 hr. There was no detectable exotherm under these conditions.

The bulk material was recovered by filtration, and the crude product washed with water until the washings were of pH 7. The water was then removed by suction, the filter cake dried by suspension in acetone (2×10 l), collected by filtration, further washed with acetone (2×10 l), and finally dried at 80° C. for a total of 72 hr. A total of 3.78 kg anhydrous material was obtained. Elemental analysis of the recovered solid shows there to be N present in the expected ratio.

CHN analysis: Found % C: 46.60; H, 6.60; N, 2.16. C: 46.52; H, 6.54; N, 2.13.

This experiment was repeated three times on approximately the same scale to provide a total of 11.9 kg of dried sample of the cyanoethyl ether of cellulose.

Reduction of cyanoethyl cellulose to aminopropyl cellulose:

A dry sample of cyanoethyl cellulose powder as above was purged under dry nitrogen, treated cautiously with a solution of borane/tetrahydrofuran complex (1M) in THF (14 l), stirred for 1 hr at room temperature, and then cautiously warmed to gentle reflux for a total of 24 hr. The cooled solution was very cautiously treated aqueous ethanol (10%, 1 l) with external ice-water cooling, and some evolution of hydrogen was detected. The wet slurry was then filtered and the wet filter cake slurried in HCl (1M, 12 l) for a total of 30 min, recovered by filtration, and re-suspended in (1M, 12 l) for a total of 1 hr. The product was collected by filtration, washed extensively with water until the washings were of pH 7, and then sucked dry. This filter cake was then slurried in ethanol (10 l), collected by filtration and sucked dry for a total of 1 hr. This cake was then slurried with ether (10 l), the product collected by filtration, sucked dry overnight at room temperature and was finally dried at 50° C. to constant weight.

Analysis of the free amine content by standard methods revealed an amine content of 0.50 mmole/g dry weight.

This experiment was also repeated for a total of three times to provide a total of 13.24 kg of dry powder.

Protection of the amino group to give Boc-aminopropyl cellulose:

A solution of sodium carbonate (1.26 kg) in water (1 l) was diluted with THF (12. l) and a sample of aminopropyl cellulose hydrochloride (4 kg) was added cautiously to avoid frothing. This was treated with di-tert butyl pyrocarbonate (4 kg) and the mixture was allowed to stand at room temperature for one week. The solid material was collected by vacuum filtration, washed with water until the washings were of pH 7, then slurried in acetone (10 l), and collected by filtration. This slurry treatment of the collected solid was then repeated (10 l). The product was finally collected by filtration, sucked to dryness and dried overnight at 80° C. under vacuum. This gave a colourless solid 4.2 kg.

This experiment was then repeated three times to provide a total weight of the N-protected derivative of 13.06 kg. This showed a residual moisture content of approximately 15%, which could have been removed by extremely vigorous drying. However, such removal was unnecessary for the next step in the procedure.

Preparation of bulk scale Boc-aminopropyl cellulose paper sheet:

Blank paper fibre in the form of long staple raw cellulose (27.8 kg) was slurried in a large volume of water (2600 liters) for a total of 20 min. This slurry was combined with the sample of powdered Boc-aminopropyl cellulose (13.06 kg) and further slurried for a total of 10 min to achieve adequate dispersion. A polyamide epichlorohydrin cross-linking agent (1.14 l) was added, and the paper slurry was then prepared in sheet form by conventional means. This produced a finished roll of paper of approximately 28 kg in weight.

Deprotection of the Boc-aminopropyl cellulose sheet:

A sample of the Boc-aminopropyl cellulose sheet of A4 size was suspended in a solution of trifluoroacetic acid in solution of dichloromethane (50%, 30 ml), for a total of 30 min. The paper was then washed with dimethylformamide (DMF) to remove excess TFA, with methanol (×1), neutralized (1M NaOH), washed water, methanol and then dichloromethane and finally dried at 40° C. under vacuum for a total of 1 hr.

This paper was assayed for free amine content by a known method using picric acid, which showed a reproducible free amine level in the range of 2–3 nmoles/mm$^2$.

Preparation of Lys-Tyr-Lys and Thr-Tyr-Ser on amine-functionalised paper:

Fmoc-O-t-butyl-Ser Derivatisation:

A sample of the above described amine functionalised paper (two sheets of dimensions 210×197 mm, of 2.85 nmoles/mm$^2$, or 0.18 mmole total amine content) indelibly marked with indicia was derivatised by reaction with 2,4-dichlorophenyl-4-(N-α-Fmoc-O-tert-butyl-Serinyloxymethyl) phenoxyacetate (650 mg or 2.7 times excess) in DMF solution for a period of 17 hr at room temperature following the general method given by Bernatowicz et al. (Tetrahedron Letters 1989, 30: 4341). The paper was washed with DMF to remove reagents (×3), dichloromethane (×6) and was then dried at room temperature under vacuum.

Determination of free amine content indicated that the degree of coupling in this reaction was of the order of 85%.

Residual amine groups were acetylated using a solution of acetic anhydride (4 ml), collidine (6 ml) and 4-dimethylaminopyridine (2 g) in acetonitrile (20 ml) for 1 hr at room temperature. The paper was then washed with acetonitrile (×3), dichloromethane (×6), and dried under vacuum.

Deprotection of the Fmoc group was achieved using a standard method utilising a solution of piperidine (15 ml) in dichloromethane (5 ml) for 30 min at room temperature. Washing of the paper with DMF (×2) and dichloromethane (×6), followed by drying under vacuum gave the material ready for the next coupling.

α-Fmoc-ω-Boc-Lys Derivatisation:

A sample of the same amine derivatised paper of identical dimensions indelibly identified with indicia was derivatised in an identical fashion using instead the analogous derivative of α-Fmoc-ω-Boc-Lys.

Residual amine acetylation and deprotection prior to the further functionalisation were performed in a manner identical to that described above.

Coupling of the second monomer (Fmoc-O-t-butyl-Tyr):

The two above monomerically linked pieces of paper were placed in one vessel and treated with a five-fold excess of a solution of the HOBt ester of Fmoc-Tyr-O-t-butyl ether which was prepared by pre-activation of a solution of Fmoc-O-t-butyl-Tyr (3.47 g, 7.56 mmol), HOBt (1.02 g, 7.56 mmol), TBTU (2.42 g, 7.56 mmol) and Hunig's Base (2.64 ml, 15.12 mmol) in DMF (160 ml) for a period of 30 min. This preformed ester solution was then reacted at room temperature overnight with the paper samples. The pieces of paper were then washed with DMF (×3) to remove reagents, dichloromethane (×6), and dried under vacuum.

Residual amine groups were acetylated using a solution of acetic anhydride (4 ml), collidine (6 ml) and 4-dimethylaminopyridine (2 g) in acetonitrile (20 ml) for 1 hr at room temperature. The paper was then washed with acetonitrile (×3), dichloromethane (×6), and dried under vacuum.

Deprotection of the Fmoc group was achieved using a standard method utilising a solution of piperidine (15 ml) in DMF (15 ml) per sheet for 30 min at room temperature. Washing of the paper with DMF (×4) and dichloromethane (×6), followed by drying of the paper under vacuum gave the material ready for the next coupling.

Coupling of the third monomer:

The sample of paper bearing Tyr-Ser was further reacted separately with a sample of the HOBt ester of Fmoc-Thr-O-t-butyl ether prepared by pre-activation of a solution of Fmoc-Thr-O-t-butyl ether (1.5 g, 3.78 mmol), HOBt (0.51 g, 3.78 mmol), TBTU (1.21 g, 3.78 mmol) and Hunig's Base (1.31 ml, 7.56 mmol) in DMF (85 ml) for a period of 30 min. The paper was reacted at room temperature overnight.

The sample of paper bearing Tyr-Lys was further reacted separately with a sample of the HOBt ester of α-Fmoc-Boc-Lys prepared by pre-activation of a solution of α-Fmoc-Boc-Lys (1.77 g, 3.78 mmol), HOBt (0.51 g, 3.78 mmol), TBTU (1.21 g, 3.78 mmol) and Hunig's Base (1.31 ml, 7.56 mmol) in DMF (85 ml) for a period of 30 min. The paper was reacted at room temperature overnight with this preformed solution.

The two pieces of paper were then washed with DMF (×2) to remove reagent, dichloromethane (×3), and dried under vacuum. Residual amine groups were acetylated using a solution of acetic anhydride (4 ml), collidine (6 ml) and 4-dimethylaminopyridine (2 g) in acetonitrile (20 ml) per sheet for 1 hr at room temperature. The paper was then washed with acetonitrile (×4), dichloromethane (×4), and dried under vacuum.

Final deprotection of the Fmoc group was achieved using a standard method utilising a solution of piperidine (15 ml) in DMF (15 ml) per sheet for 30 min at room temperature. Washing of the paper with DMF (×4) and dichloromethane (×6) followed by drying of the paper under vacuum gave the material ready for the final cleavage.

Cleavage of the trimers from the paper:

The sample of paper bearing Thr-Tyr-Ser was cut into small portions, treated with TFA/H$_2$O (95:5, 89.25 ml) and stored at room temperature overnight. Solid material was removed by filtration and washed with dichloromethane (×2) and methanol (×2), and the filtrates combined. Acid was removed by evaporation below 40° C., and the sample freed from acid by azeotropy from toluene/dichloromethane (×2). The sample was dissolved in water (15 ml), filtered, and freeze dried. The mass recovery was essentially quantitative. This was examined by hplc analysis and the desired material was shown to be the major product by comparison with a genuine sample, and moreover exhibited identical m/e peaks in the mass spectrum.

The sample of paper bearing Lys-Tyr-Lys was cut into small portions, treated with TFA/H$_2$O (95:5, 89.25 ml) and stored at room temperature overnight. Solid material was removed by filtration, washed with dichloromethane (×2) and methanol (×2), and the filtrates combined. Acid was removed by evaporation below 40° C., and the sample freed from acid by azeotropy from toluene/dichloromethane (2 x). The sample was dissolved in water (15 ml), filtered and freeze dried. The mass recovery was essentially quantitative. This was examined by hplc analysis and the desired material was shown to be the major product by comparison with a genuine sample, and moreover exhibited the desired m/e peak in the mass spectrum.

Preparation of a 1677 component peptoid library for biological screening:

Three sheets of amine functionalised paper as described above of dimensions 210×297mm were indelibly marked with a pattern of indicia (43 columns and 39 rows), and subsequently deprotected with TFA in the manner described above ready for the coupling of the first monomers. Analysis revealed the presence of 1.9 nmol/mm$^2$ of amine groups.

Functionalisation of the sheet:

Each of the 43 columns of paper was divided from the original sheet and separately functionalised as follows: Each column of paper was treated with an individual Fmoc-protected amino acid derivative pre-activated as its 2,4-dichlorophenyl 4-(oxymethyl) phenoxy acetate as described above in a solution of DMF (0.5 ml) and pyridine (10 ml) at room temperature overnight. The paper was washed with DMF (×4) and dichloromethane (×5) and dried at 40° C. for 30 min. Acetylation of residual amine functionality was carried out as described above.

Deprotection of the amine groups was also carried out as described above.

Coupling of the second monomer:

The complete set of stacked strips of reaction zones of the original paper sheets was assembled into one block and then cut again at right angles to the original cutting direction into individual reaction zones. Each set of individual reaction zones from a complete row was then coupled with a second Fmoc-protected monomeric unit, pre-activated as its 2,4-dichlorophenyl 4-(oxymethyl)phenoxy acetate ester as described above. On completion of reaction, these individual reaction zones were washed, acetylated, and finally the Fmoc protection group was removed as described above.

Coupling of the third monomer:

The complete set of 1677 individual reaction zones charged with dimeric amine derivatives were combined into one vessel, and reacted with diphenylacetyl chloride (2.31 g, 0.1 mol), with Hunig's Base (3.5 ml, 0.1 mol) in DMF (96.5 ml) at room temperature overnight. The set of individual reaction zone was washed with DMF (×3), and dichloromethane (×4) and dried at 40° C. for 30 min under vacuum. To remove all extraneous reagents, the complete set of reaction zones was treated in a Soxhlet extractor with dichloromethane overnight, and the extract discarded. The reaction zones were dried at 40° C. under vacuum for three hours.

Cleavage of individual trimeric products:

The trimeric products were removed from the paper in the following manner: Each individual labelled reaction zone was separated and treated with TFA/H$_2$O (95:5, 50 ml) at room temperature overnight. Each reaction zone was then washed with dichloromethane (12×50 ml), methanol (4×50 ml), the washings being combined and evaporated under nitrogen. Analysis of individual products is exemplified by the following: After cleavage from the paper support, individual trimeric products were identified by the indicia marked thereon. A subset of these was examined by both hplc and mass spectrometry and, in the cases examined, confirmed the presence of the desired compound.

Below is a subset of typical analytical data for compounds examined by mass spectrometry:

| Indicia | Structure | Expected m/e | Found m/e |
|---------|-----------|--------------|-----------|
| A3410   | 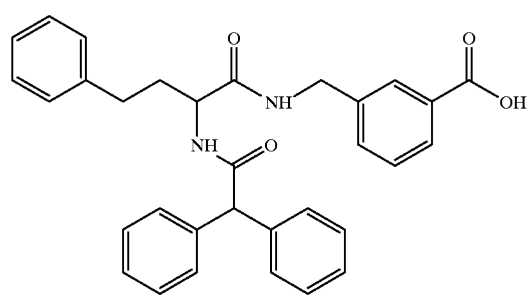          | 533.62       | 535.0     |
| B3315   | 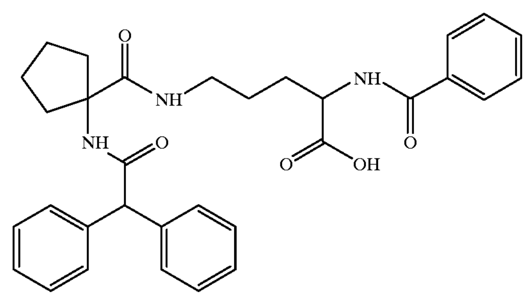          | 541.62       | 543.0     |

-continued

| Indicia | Structure | Expected m/e | Found m/e |
|---|---|---|---|
| C3702 | 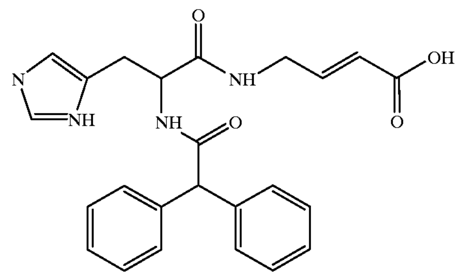 | 432.41 | 432.8 |
| A0604 | 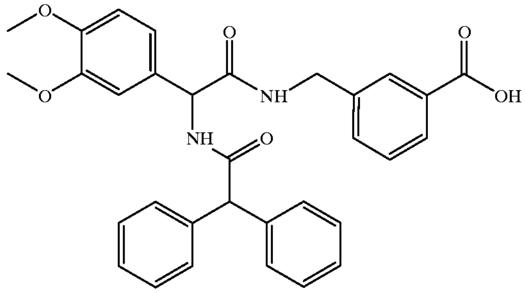 | 538.61 | 539.0 |

EXAMPLE 2

Syntheses on aminomethyl-substituted laminated resin sheet

Preparation of aminomethyl-substituted laminar sheet:

A sample of 100 g of a partially cross-linked aminomethyl polystyrene resin (Novabiochem 01-640010) was thoroughly mixed with a sample of low melting thermoplastic polyethylene glue (Dritex DT157/300) and the mixture was evenly spread over the surface of a portion of non-woven fibrous polypropylene sheet (Freudenberg Lutrasil 4150) of area 16 square meters. A further sheet of the same non-woven fibrous polypropylene sheet of identical area was then superimposed onto the bottom loaded sheet, and the two were then heat welded together (within a temperature range of 90–140° C.) to give a single material containing resin in which amino groups were demonstrably available.

Titrimetric analysis of the free amine content showed that, in this example, free amine density was 2.2 nmole/mm$^2$.

Fmoc-O-t-butyl-Ser Derivatisation:

A sample of the above polypropylene cloth (210×145 mm, or 67.8 mmole total amine content), indelibly identified with indicia, was derivatised by reaction with the 2,4-dichlorophenyl N-α-Fmoc-O-t-butyl-Ser-4-oxymethylphenoxyacetate ester (258 mg or 5 times excess) in DMF solution for a period of 17 hr at room temperature. The resin cloth was washed with DMF (×-3) to remove reagents and dichloromethane (×3), and was then dried at room temperature under vacuum.

Residual amine groups were acetylated using a solution of acetic anhydride (4 ml), collidine (6 ml) and 4-dimethylaminopyridine (2 g) in acetonitrile (20 ml) for 1 hr at room temperature. The resin cloth was then washed with acetonitrile (×3), dichloromethane (×6), and dried under vacuum.

Deprotection of the Fmoc group was achieved using a standard method utilising a solution of piperidine (10 ml) in DMF (10 ml) for 30 min at room temperature. Washing of the cloth with DMF (×4) and dichloromethane (×6), followed by drying under vacuum gave the material ready for the next coupling.

Fmoc-α-Boc-Lys Derivatisation:

A sample of the same polypropylene cloth of identical dimensions, indelibly identified with indicia, was derivatised in an identical fashion using instead the analogous derivative of Fmoc-α-Boc-Lys.

Residual amine acetylation, and deprotection prior to further functionalisation were performed in a manner identical to that described above.

Coupling of the second monomer:

The two above monomerically linked pieces of resin cloth were combined in one vessel and treated with a five-fold excess of a solution of the HOBt ester of Fmoc-O-t-butyl Tyr prepared by pre-activation of a solution of Fmoc-O-t-butyl Tyr (331 mg, 0.68 mmol), HOBt (92 mg, 0.68 mmol), TBTU (217 mg, 0.68 mmol) and Hunig's Base (120 ml, 0.68 mmol) in DMF for a period of 30 min. This pre-activated ester was then reacted with the pieces of resin cloth at room temperature overnight. The two pieces of resin cloth were then washed with DMF (×3) to remove reagents, dichloromethane (×6), and dried under vacuum.

Residual amine groups were acetylated using a solution of acetic anhydride (4 ml), collidine (6 ml), and 4-dimethylaminopyridine (2 g) in acetonitrile (20 ml) for 1 hr at room temperature. The resin cloth was then washed with acetonitrile (×3) and dichloromethane (×6), and dried under vacuum.

Deprotection of the Fmoc group was achieved using a standard method utilising a solution of piperidine (10 ml) in DMF (10 ml) for 30 min at room temperature. Washing of the cloth with DMF (×4) and dichloromethane (×6), followed by drying of the resin cloth under vacuum, gave the material ready for the next coupling.

Coupling of the third monomer:

The sample of resin cloth bearing Tyr-Ser was further reacted separately with a sample of the HOBt ester of Fmoc-O-t-butyl-Thr prepared by pre-activation of a solution of Fmoc-O-t-butyl Thr (134 mg, 0.339 mmol), HOBt (46 mg, 0.339 mmol), TBTU (108 mg, 0.339 mmol) and Hunig's Base (60 ml, 0.339 mmol) in DMF (10 ml) for a period of 30 min. The resin cloth was reacted at room temperature overnight with this preformed reagent.

The sample of resin cloth bearing Tyr-Lys was further reacted separately with a sample of the HOBt ester of α-Fmoc-Boc-Lys prepared by pre-activation of a solution of α-Fmoc-Lys (159 mg, 0.339 mmol), HOBt (46 mg, 0.339), TBTU (108 mg, 0.339 mmol) and Hunig's Base (60 ml, 0.339 mmol) in DMF (10 ml) for a period of 30 min. The resin cloth was reacted at room temperature overnight with this preformed reagent.

The two pieces of resin cloth were then washed with DMF (×3) to remove reagents, dichloromethane (×6), and dried under vacuum.

Residual amine groups were acetylated using a solution of acetic anhydride (4 ml), collidine (6 ml) and 4-dimethylaminopyridine (2 g) in acetonitrile (20 ml) for 1 hr at room temperature. The resin cloth was then washed with acetonitrile (×3), dichloromethane (×6), and dried under vacuum.

Final deprotection of the Fmoc group was achieved using a standard method utilising a solution of piperidine (10 ml) in DMF (10 ml) for 30 min at room temperature. Washing of the cloth with DMF (×4) and dichloromethane (×6), followed by drying under vacuum, gave the material ready for the final cleavage.

Cleavage of the trimers from the resin cloth:

The sample of resin cloth bearing Thr-Tyr-Ser was separately treated with TFA/H$_2$O (95:5, 30 ml) and stored at room temperature overnight. The acid solution was removed from the cloth by filtration, was removed by evaporation below 40° C., and the sample freed from acid by azeotropy from toluene/dichloromethane (3 x). The mass recovery was essentially quantitative and the presence of the desired product was confirmed by hplc and ms analysis.

The sample of resin cloth bearing Lys-Tyr-Lys was separately treated with TFA/H$_2$O (95:5, 30 ml) and stored at room temperature overnight. The acid was removed by evaporation below 40° C., and the sample freed from acid by azeotropy from toluene/dichloromethane (3 x). Again, the mass recovery was essentially quantitative and formation of the desired product was confirmed by hplc and ms analysis.

Preparation of a 27 component tripeptide library on resin cloth for biological screening:

Derivatisation with the first monomer (using α-Fmoc-ωn-Boc-Lys, Fmoc-Ser-O-t-butyl ether and Fmoc-Leu):

Three samples of the above polypropylene resin cloth (each 210×150 mm, or 68.7 mmol total amine content), each having reaction zones indelibly identified in a 3×3 grid pattern of indicia, were derivatised separately by reaction in DMF solution for a period of 17 hr at room temperature with 2,4-dichlorophenyl-α-Fmoc-aminoacyl-4-oxymethylphenoxyacetate (0.34 mmol or 5 times excess) derivatives of the amino acid monomers listed above. The resin cloth was washed with DMF solution (×3) to remove reagents, dichloromethane (×5) and was then dried at room temperature under vacuum for 15 min.

Residual amine groups were acetylated on the whole set of sheets using a solution of acetic anhydride (6 ml), collidine (9 ml) and 4-dimethylaminopyridine (3 g) in acetonitrile (30 ml) for 1 hr at room temperature. The resin cloth was then washed with acetonitrile (×4) and dichloromethane (×6), and dried under vacuum for 1 hr.

Deprotection of the Fmoc group was achieved using a standard method utilising a solution of piperidine (15 ml) in DMF (15 ml) for 30 min at room temperature. Washing of the cloth with DMF (×4) and dichloromethane (×6), followed by drying of the cloth under vacuum, gave the material ready for the next coupling.

Derivatisation with the second monomers (using FmocTyr-O-t-butyl ether, FmocSer-O-t-butyl ether and Fmoc Phe):

The original sheets were divided into three columns, and each set of three columns of three reaction zones was reacted separately with the second monomer. Each of the nine monomerically linked pieces of resin cloth in three columns was combined in one vessel and treated with a five-fold excess of a solution of the HOBt ester of the above Fmoc-amino acid preformed from Fmoc-amino acid (0.343 mmol, 5 times excess), HOBt (46 mg, 0.343mmol), TBTU (108 mg, 0.343 mmol) and Hunig's Base (60 ml, 0.343 mmol) by reaction in DMF (10 ml) for a period of 30 min. This was then reacted at room temperature overnight with the samples of resin cloth. The pieces of resin cloth were then washed to remove reagents using DMF (×3), dichloromethane (×5), and dried under vacuum at room temperature for 15 min.

Residual amine groups were acetylated using a solution of acetic anhydride (6 ml), collidine (9 ml) and 4-dimethylaminopyridine (3 g) in acetonitrile (30 ml) for 1 hr at room temperature. The resin cloth was then washed with acetonitrile (×4), dichloromethane (×6), and dried under vacuum for 1 hr.

Deprotection of the Fmoc group was achieved using a standard method utilising a solution of piperidine (15 ml) in DMF (15 ml) for 30 min at room temperature. Washing of the cloth with DMF (×4) and dichloromethane (×6) followed by drying of the resin cloth under vacuum gave the material ready for the final coupling.

Coupling of the third monomers (using FmocThr-O-t-butyl ether, αFmoc-ω-Boc-Lys and Fmoc-Gly):

The samples of resin cloth were divided into their individual portions by cutting in a direction orthogonal to the first cut. Each set of samples of resin cloth bearing dimeric units was further reacted separately with a sample of the HOBt-ester of Fmoc-amino acids as listed above, prepared by pre-activation of a solution of Fmoc-amino acid (0.343 mmol), HOBt (46 mg, 0.343 mmol), TBTU (108 mg, 0.343 mmol) and Hunig's Base (60 ml, 0.343 mmol) in DMF (10 ml) for a period of 30 min. The resin cloth was then reacted at room temperature overnight with this pre-activated reagent. Each individual piece of resin cloth was then washed to remove reagents with DMF (×3) and dichloromethane (×6), and dried under vacuum.

Residual amine groups were acetylated using a solution of acetic anhydride (6 ml), collidine (9 ml) and 4-dimethylaminopyridine (3 g) in acetonitrile (30 ml) for 1 hr at room temperature. The resin cloth was then washed with acetonitrile (×4), dichloromethane (×6), and dried under vacuum.

Final deprotection of the Fmoc group was achieved using a standard method utilising a solution of piperidine (15 ml) in DMF (15 ml) for 30 min at room temperature. Washing of the cloth with DMF (×4) and dichloromethane (×6), followed by drying under vacuum, gave the material ready for the final cleavage.

Cleavage of trimers from the resin cloth:

Each sample of resin cloth bearing an individual trimeric unit was separately treated with TFA/H$_2$O (95:5, 2 ml) and stored at room temperature overnight. The cloth was separated by filtration, and washed with dichloromethane (2 ml×12), methanol (2 ml×4), and the washings combined. The acid was removed by evaporation below 40° C., and the sample freed from acid by azeotropy from toluene/ dichloromethane (3 x). The mass recovery was essentially quantitative and formation of the desired products was confirmed by hplc and ms analysis in comparison with an authentic sample. Results are given below:

| Entry number | Structure | Expected m/e | Found m/e |
|---|---|---|---|
| 1 | ThrTyrLys | 410.46 | 411.0 |
| 2 | LysTyrLys | 437.56 | 438.2 |
| 3 | GlyTyrLys | 366.46 | 367.3 |
| 4 | ThrPheLys | 394.46 | 395.6 |
| 5 | LysPheLys | 421.56 | 422.5 |
| 6 | GlyPheLys | 350.46 | 351.7 |
| 7 | TheSerLys | 334.46 | 335.0 |
| 8 | LysSerLys | 361.46 | 362.6 |
| 9 | GlySerLys | 290.36 | 291.5 |
| 10 | ThrTyrSer | 369.36 | 370.0 |
| 11 | LysTyrSer | 396.46 | 396.9 |
| 12 | GlyTyrSer | 325.36 | 326.6 |
| 13 | ThrPheSer | 353.36 | 354.1 |
| 14 | LysPheSer | 380.46 | 381.4 |
| 15 | GiyPheSer | 309.36 | 309.8 |
| 16 | ThrSerSer | 292.90 | 294.2 |
| 17 | LysSerSer | 320.36 | 321.3 |
| 18 | GlySerSer | 249.26 | 250.4 |
| 19 | ThrTyrLeu | 395.46 | 395.8 |
| 20 | LysTyrLeu | 422.56 | 423.3 |
| 21 | GlyTyrLeu | 351.46 | 352.1 |
| 22 | ThrPheLeu | 379.46 | 380.1 |
| 23 | LysPheLeu | 406.56 | 407.1 |
| 24 | GlyPheLeu | 335.46 | 336.6 |
| 25 | ThrSerLeu | 319.36 | 320.6 |
| 26 | LysSerLeu | 346.46 | 347.5 |
| 27 | GlySerLeu | 275.36 | 276.1 |

Preparation on resin cloth of a 1677 component library for biological screening:

Three sheets of the polypropylene resin cloth described above of dimensions 210×297mm were indelibly marked with a pattern of indicia (43 columns and 39 rows), ready for the coupling of the first monomers. Analysis revealed the presence of 2.18 nmol/mm$^2$ of amine groups.

Functionalisation of the sheet:

Each column of polypropylene resin cloth was divided from the original sheet, and separately functionalised by treatment with an individual Fmoc protected amino acid derivative pre-activated as its 2,4-dichlorophenyl 4-(oxymethyl)phenoxy acetate as described above in a solution of DMF (0.5 ml) and pyridine (10 ml) at room temperature overnight. The cloth strips were washed with DMF (×4) and dichloromethane (×5) and dried at 40° C. for 30 min. Acetylation of residual amine functionality was carried out as described above.

Deprotection of the amine groups was also carried out as described above.

Coupling of the second monomer:

The complete set of columns of the original polypropylene resin sheets was assembled into one block and cut into individual pieces. Each set of pieces from individual rows was then coupled with a second Fmoc-protected monomeric unit, pre-activated as its 2,4-dichlorophenyl 4-(oxymethyl) phenoxy acetate ester as described above. Upon completion of reaction, these were washed, acetylated and, finally, the Fmoc protection group was removed as described above.

Coupling of the third monomer:

The complete set of 1677 individual dimeric amine derivatives was reacted with diphenylacetyl chloride (2.31 g, 0.1 mol) and Hunig's Base (3.5 ml, 0.1 mol) in DMF (96.5 ml) at room temperature overnight in smaller subsets. Each set of polypropylene resin cloth pieces was washed with DMF (×3), dichloromethane (×4) and dried at 40° C. for 30 min under vacuum.

Cleavage of individual trimeric products from the polypropylene cloth:

Individual labelled resin cloth pieces were separated and treated with TFA/H$_2$O (95:5, 50 ml) at room temperature overnight. Each was then washed with acetonitrile/water (1:1, 3×100 ml), the washings combined and evaporated under vacuum centrifugation. After cleavage from the resin cloth support, individual trimeric products were identified by the indicia marked thereon. A subset of these was examined by both hplc and mass spectrometry and, in the cases examined, confirmed the formation of the desired compounds.

A subset of typical analytical data for compounds examined by mass spectrometry is given below:

| Indicia | Structure | Expected m/e | Found m/e |
|---|---|---|---|
| B3412 | 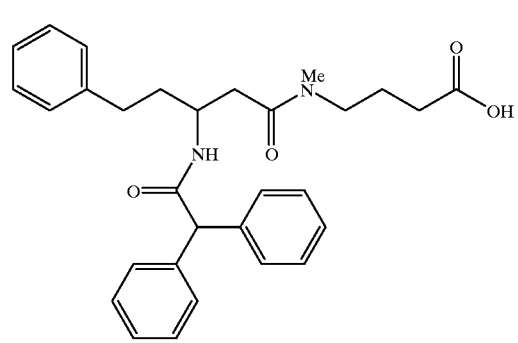 | 487.59 | 487.00 |

-continued

| Indicia | Structure | Expected m/e | Found m/e |
|---|---|---|---|
| B2412 | 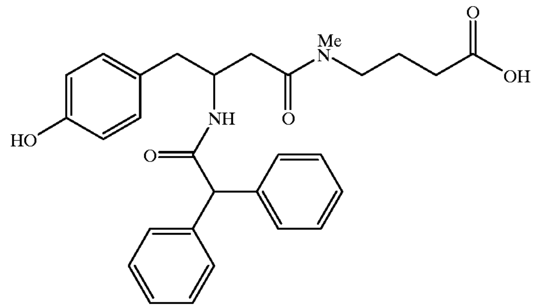 | 458.54 | 475.0* |
| C3408 | 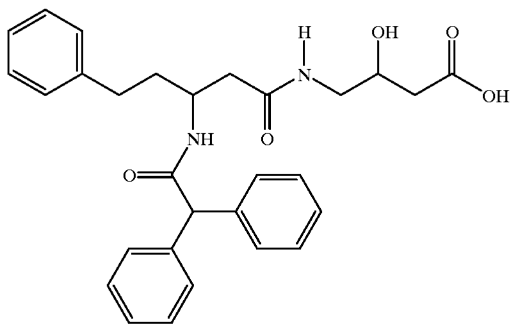 | 488.57 | 489.00 |
| A3408 | 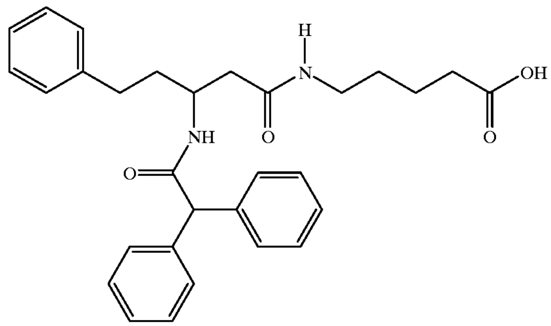 | 486.59 | 505.1* |

*MNH⁴⁺

The choice of resins is not limited to the single form specified in the foregoing example. The laminar sheet may be prepared from a wide range of alternative resins. It will be appreciated that different types of resin permit differing types of chemistry to be carried out, some of which are exemplified, but not limited, by the following:

The preparation of oligosaccharides is conveniently carried out on a polymeric (ethylene glycol) ω-monomethyl ether, (see Douglas, S. P., Whitfield, D. M., Krepinsky, J. J, J. Amer. Chem. Soc., 1995, 117, 2116) or alternatively on a poly(p-(propen-3-OH-1-yl)) linked polystyrene.

Preparation of a series of serine phosphopeptides was carried out on Wang resin (see Shapiro, G., Swoboda, R., Stauss, U., Tetrahedron Letters, 1994, 35, 869).

Tentagel resin has been found to be useful for the formation of C-C bonds such as the Heck reaction, (see Hiroshauge, M, Hauske, J. R., Zhou, P., Tetrahedron Letters, 1995, 36, 4567) and other C—C bond forming processes such as the Stille reaction may be conveniently carried out on Rink amide functionalised polystyrene, (see Forman, F. W., Sucholeiki, I., J. Org. Chem., 1995,60,523).

A series of aspartic acid protease inhibitors has been prepared on a dihydropyran functionalised resin, (see Kick, E. K., Ellman, J. A., J. Med. Chem., 1995,38,1427) and examples of aryl ether formation via the Mitsonobu reaction have been successfully carried out on Tentagel S RAM Fmoc resin, (see Rano, T. A., Chapman, K. T., Tetrahedron Letters, 1995,36,3789).

It will be appreciated by those skilled in the art that there are many further examples in the literature of alternative resins suitable for still further chemistry to be carried out.

What is claimed is:

1. A method of making a library of compounds comprising the steps of:
  (a) individually identifying a plurality of discrete reaction zones on a laminar solid support material comprising a layer of a particulate, functionalized solid support resin affixed to a porous, inert, laminar material;
  (b) charging each of said reaction zones with a starting material;
  (c) sub-dividing the material to define at least two initial batches of reaction zones, wherein said batches are separated from one another;
  (d) applying at least two different reagents, one to each of the reaction zones in each initial batch, and recording the identity of those reaction zones to which each of said different reaction reagents is applied;

(e) subjecting all reaction zones to reaction conditions which promote reaction to completion;

(f) further sub-dividing each of said at least two initial batches into at least two alternative batches wherein said at least two alternative batches are separated from one another;

(g) applying at least two different reagents, one to each of the reaction zones in each alternative batch, and recording the identity of those reaction zones to which each of said different reagents is applied;

(h) subjecting all reaction zones to reaction conditions which promote reaction to completion; and (i) repeating steps (f) to (h) inclusive from zero to n times, as desired, wherein n is a whole number integer.

2. The method claim 1 wherein the resin is sandwiched between two layers of a porous, inert, laminar material.

3. The method of claim 1 wherein the resin comprises cross-linked polystyrene resin containing amino groups.

4. The method of claim 1 wherein the laminar solid support material is provided in the form of a sheet.

5. The method of claim 4 wherein the laminar solid support material is provided in the form of a plurality of sheets and a plurality of discrete reaction zones is defined on each of said sheets.

6. The method of claim 4 wherein in step (b), each sheet is charged with a different starting material.

7. The method of claim 4 wherein each sheet is sub-divided such that each sheet defines at least two initial batches of reaction zones, wherein each of said initial batches is separated from one another.

8. The method of claim 1 wherein the compounds obtained at the end of step (i) are linked to the laminar solid support material by linker groups which are cleavable by acidic, basic or hydrogenolytic chemical reagents, by a combination of one or more or the foregoing chemical reagents, by light induced cleavage, or by a combination of one or more of the foregoing chemical reagents and light induced cleavage.

9. The method of claim 1 wherein the reagents applied in step (d) are selected from the group consisting of: amino acids, nucleotides, sugars, heterocycles, lipids and combinations thereof.

10. The method of claim 1 wherein the reactions zones are identified by application of indicia selected from the group consisting of: numbers, letters, symbols, colors, Smiles strings, bar-codes, chemical structures, marked or printed punch cards, ultraviolet-readable systems and electromagnetically-readable systems.

11. The method of claim 1 wherein the laminar solid support material is present as a cloth comprising a layer of crosslinked polystyrene resin containing amino groups affixed to, and sandwiched between, two layers of porous polypropylene.

12. A method of making a library of compounds comprising the steps of:

(a) providing a plurality of sheets of a solid support material to which compounds may be releasably bound, each such sheet bearing indicia identifying a plurality of individual reaction zones arranged in rows and columns in a two-dimensional array, said solid support material comprising a layer of a particulate, functionalized solid support resin affixed to a porous, inert, laminar material;

(b) treating each sheet with respective first reagents to bind respective first constituents to each of the individual reaction zones on the sheets;

(c) superposing the sheets resulting from step (b) to form a block and repeatedly subdividing the block parallel to one of its faces to form a plurality of stacks of strips derived from respective divided sheets, each strip bearing one of said rows of reaction zones;

(d) treating each of the stacks of strips resulting from step (c) with respective second reagents to bind respective second constituents to the first constituents on the strips to form growing compounds;

(e) reassembling the treated stacks of strips resulting from step (d) to reform the block and dividing the reformed block parallel to a second face thereof superposed at right angles to said first face so that each strip is divided into stacks of individual reaction zones; and (f) treating each of the stacks of individual reaction zones resulting from step (e) with respective third reagents to bind respective third constituents to the growing compounds already bound on the reaction zones to form stacks of treated individual reaction zones.

13. The method of claim 12 wherein the stacks of treated individual reaction zones resulting from step (f) are further reassembled and divided and are thereafter treated with respective fourth reagents to bind respective fourth constituents to the growing substrate already bound on the reaction zones, and optionally repeating such further reassembly, division and treatment steps as many times as are desired.

14. The method claim 12 wherein the resin is sandwiched between two layers of a porous, inert, laminar material.

15. The method of claim 12 wherein the resin comprises cross-linked polystyrene resin containing amino groups.

16. The method of claim 12 wherein the compounds obtained at the end of step (f) are linked to the solid support material by linker groups which are cleavable by acidic, basic or hydrogenolytic chemical reagents, by a combination of one or more or the foregoing chemical reagents, by light induced cleavage, or by a combination of one or more of the foregoing chemical reagents and light induced cleavage.

17. The method of claim 12 wherein the reagents applied in steps (b), (d) and (f) are selected from the group consisting of: amino acids, nucleotides, sugars, heterocycles, lipids and combinations thereof.

18. The method of claim 12 wherein the reactions zones are identified by application of indicia selected from the group consisting of: numbers, letters, symbols, colors, Smiles strings, bar-codes, chemical structures, marked or printed punch cards, ultraviolet-readable systems and electromagnetically-readable systems.

19. The method of claim 12 wherein the laminar support material is present as a cloth comprising a layer of crosslinked polystyrene resin containing amino groups affixed to, and sandwiched between, two layers of porous polypropylene.

* * * * *